(12) United States Patent
Martinez et al.

(10) Patent No.: US 7,541,197 B2
(45) Date of Patent: Jun. 2, 2009

(54) PLANAR OPTICAL WAVEGUIDE BASED SANDWICH ASSAY SENSORS AND PROCESSES FOR THE DETECTION OF BIOLOGICAL TARGETS INCLUDING PROTEIN MARKERS, PATHOGENS AND CELLULAR DEBRIS

(75) Inventors: Jennifer S. Martinez, Santa Fe, NM (US); Basil I. Swanson, Los Alamos, NM (US); Karen M. Grace, Los Alamos, NM (US); Wynne K. Grace, Los Alamos, NM (US); Andrew P. Shreve, Santa Fe, NM (US)

(73) Assignee: Los Alamos National Security, LLC, Los Alamos, TX (US)

( * ) Notice: Subject to any disclaimer, the term of this patent is extended or adjusted under 35 U.S.C. 154(b) by 380 days.

(21) Appl. No.: 11/172,246

(22) Filed: Jun. 29, 2005

(65) Prior Publication Data
US 2006/0019244 A1    Jan. 26, 2006

Related U.S. Application Data

(60) Provisional application No. 60/583,911, filed on Jun. 29, 2004.

(51) Int. Cl.
*G01N 33/551*    (2006.01)
(52) U.S. Cl. ............... 436/524; 422/82.05; 422/82.11; 435/5; 435/6; 435/7.2; 435/287.2; 435/288.7; 436/164; 436/172; 436/805

(58) Field of Classification Search .............. 422/82.05, 422/82.11; 435/5, 6, 7.2, 287.2, 288.7; 436/164, 436/172, 524, 805
See application file for complete search history.

(56) References Cited

U.S. PATENT DOCUMENTS 5,830,766 A  *  11/1998   Attridge et al. .............. 436/518

* cited by examiner

*Primary Examiner*—Christopher L Chin
(74) *Attorney, Agent, or Firm*—Bruce H. Cottrell; Juliet A. Jones

(57) ABSTRACT

An assay element is described including recognition ligands bound to a film on a single mode planar optical waveguide, the film from the group of a membrane, a polymerized bilayer membrane, and a self-assembled monolayer containing polyethylene glycol or polypropylene glycol groups therein and an assay process for detecting the presence of a biological target is described including injecting a biological target-containing sample into a sensor cell including the assay element, with the recognition ligands adapted for binding to selected biological targets, maintaining the sample within the sensor cell for time sufficient for binding to occur between selected biological targets within the sample and the recognition ligands, injecting a solution including a reporter ligand into the sensor cell; and, interrogating the sample within the sensor cell with excitation light from the waveguide, the excitation light provided by an evanescent field of the single mode penetrating into the biological target-containing sample to a distance of less than about 200 nanometers from the waveguide thereby exciting the fluorescent-label in any bound reporter ligand within a distance of less than about 200 nanometers from the waveguide and resulting in a detectable signal.

30 Claims, 5 Drawing Sheets

Fig. 5B

PLANAR OPTICAL WAVEGUIDE BASED SANDWICH ASSAY SENSORS AND PROCESSES FOR THE DETECTION OF BIOLOGICAL TARGETS INCLUDING PROTEIN MARKERS, PATHOGENS AND CELLULAR DEBRIS

This application claims the benefit of U.S. Provisional Application Ser. No. 60/583,911 filed on Jun. 29, 2004.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to sandwich assay processes and to a thin film supported sandwich assay element on a single mode planar optical waveguide. Such an assay can provide a means of detecting and quantifying proteins and the like for medical diagnostics or for environmental surveillance.

BACKGROUND OF THE INVENTION

The detection of trace amounts of biologically significant compounds, such as steroids, drugs, selected antigens, or tumor markers, is often accomplished inexpensively by the employment of an immunoassay. Enzyme immunoassay (EIA) methods are common antigen detection techniques. One of the most common types of immunoassays is the Enzyme-Linked Immunosorbant Assay (ELISA), a solid phase enzyme immunoassay technique. Such assays rely on an immunogenic recognition of a substance in question followed by the amplification of the signal generated by that recognition. Enzymes are widely used in immunoassays as the amplifier of the antibody-antigen recognition event. Traditionally, antigen capture assays involve the application of an antigen-containing sample to a plastic plate where a "capture" antibody has been previously bound. A secondary ("detection") antibody is then applied and binds to the antigen. This binding forms a sandwich that leads to the quantification of antigen present. EIAs are easy to multiplex and the use of more than one antibody in the sandwich assay improves the specificity of the test by requiring two specific interactions before signal is detected.

ELISA may be preformed in a number of different ways. The two most common are the competitive mode and the sandwich assay. In a competitive mode ELISA, a surface, usually either a polystyrene plate or a nitrocellulose membrane, is coated with a capture antigen. These surfaces are normally chosen because they bind protein non-specifically. Therefore, if the antigen is not a protein, it may be covalently linked to a carrier protein and bound to the surface without further chemistry. After the antigen is bound, the remaining binding sites on the surface are blocked with another protein as a blocking agent. Then the test fluid and enzyme-labeled antibody are added. If no antigen is in the test fluid, the labeled antibody will bind to the antigen adsorbed on the surface. Conversely, if antigen is present in the test fluid, the antigen will block the binding sites on the enzyme-labeled antibody and prevent it from binding to the antigen adsorbed on the surface. The surface is washed to remove unbound materials, and a substrate is added for the enzyme. The enzyme catalyzes a reaction in which the substrate reacts to form a colored material that can be quantitatively measured with a spectrophotometer. The intensity of the color produced is proportional to the enzyme activity and the amount of antibody bound, which is inversely proportional to the amount of antigen in the test fluid.

In a sandwich assay ELISA, an antibody that recognizes part of the antigen is bound to a surface. Since antibodies are proteins, this is readily accomplished by allowing the surface to contact a solution of the antibody. As in the competitive ELISA, the remaining sites on the surface are blocked with another protein as a blocking agent. The test fluid is then added. If an antigen is present in the test fluid, the antibody on the surface will capture the antigen. Then a second, enzyme-labeled antibody, which recognizes a different part of the antigen than the first antibody, is added. The second antibody will then bind to the antigen that is captured on the surface. After washing the surface to remove any unbound materials, a substrate for the enzyme is added and the color produced is measured spectrophotometrically. In this form of an ELISA, the signal is directly proportional to the concentration of the antigen in a test sample. Such a sandwich assay is widely used in the commercial arena, e.g., for home pregnancy tests.

In either type of ELISA, the enzyme acts as the amplifier of the antigen-antibody reaction. That is, a color or other signal, such as light from some chemiluminescent reaction, is produced that can be observed macroscopically. Without this amplification step, the sensitivity of an immunoassay would be orders of magnitude less.

Several problems occur in the use of enzymes as amplifiers in immunoassays including:

1) Any change in enzyme activity will affect the precision of the assay. For example, loss of half of the activity of the enzyme in a competitive ELISA may produce a false positive since a smaller signal indicates the presence of the test substance. Since enzyme activity is sensitive to storage conditions, enzymes must be kept either refrigerated, freeze-dried or both. Also, controls must be performed to constantly test the activity of the enzyme. Inevitably, the shelf-life is limited by the stability of the enzyme.

2) Enzymes are expensive as they are derived from living sources and require substantial processing costs. The least expensive enzyme, on an activity basis, is Horseradish Peroxidase, which is, not surprisingly, the most common enzyme used in ELISAs. However, even Horseradish Peroxidase costs about $5/mg or $5000/g. Fortunately, very little enzyme is necessary for each assay.

3) The labeling of antibodies with enzymes is often a quite laborious procedure, as one must ensure that little unbound enzyme is present. If significant amounts of unbound enzyme are present or significant amounts of unlabeled antibody are present, the sensitivity of the ELISA is reduced.

4) Enzymes are often heterogeneous materials due to their isolation from natural sources. Therefore, characterization of enzyme-antibody conjugates can be difficult.

Although EIAs performed on 96-well plates are popular in the academic lab, modem clinical labs employ more highly automated assay systems. One example is the Abbott disposable IMx® cartridge system, which utilizes fluorescent polarization. In this approach, a capture antibody is bound to a microparticle, and the sample is incubated with the filter and a fluorescently labeled detection antibody. Since the unbound detection antibody has no net fluorescent polarization compared to the bound detection antibody, the fluorescent polarization signal is proportional to the amount of bound sample. Although this assay system does not employ an enzymatic amplification step, it is still very sensitive, and it has other advantages, including the elimination of time consuming wash steps.

Other automated systems involve other approaches to save time, such as using kinetic rather than equilibrium approaches to measure product. Other detection systems include exotic methods such as electrochemiluminescence (ECL), where the capture antibody is bound to magnetic beads and the detection antibody is labeled with a $Ru(bipyridyl)_3$ complex. After incubation and washing, the ruthenium complex emits light in an electrochemical cell. This assay system can detect antigens in the low picomolar (pM) range. All the above assay systems are performed in clinical labs on expensive equipment and are not available as physician operated desktop systems with untrained professionals.

SUMMARY OF THE INVENTION

To achieve the foregoing and other objects, and in accordance with the purposes of the present invention, as embodied and broadly described herein, the present invention provides a sandwich assay sensor element including recognition ligands bound to a film on a single mode planar optical waveguide, the film from the group of a membrane, a polymerized bilayer membrane, and a self-assembled monolayer containing polyethylene glycol or polypropylene glycol groups therein.

The present invention further provides a sandwich assay process including: injecting a biological target-containing sample into a sensor cell including recognition ligands bound to a film on a single mode planar optical waveguide, the film from the group of a membrane, a polymerized bilayer membrane, and a self-assembled monolayer containing polyethylene glycol or polypropylene glycol groups therein, the recognition ligands adapted for binding to selected biological targets; maintaining the biological target-containing sample within the sensor cell for a time sufficient for a binding event to occur between selected biological targets within the sample and the recognition ligands adapted for binding to selected biological targets; injecting a solution into the sensor cell, the solution including a reporter ligand adapted for binding to bound selected biological targets; and, interrogating the biological target-containing sample within the sensor cell with excitation light from the waveguide, the excitation light provided by an evanescent field of the single mode penetrating into the biological target-containing sample to a distance of less than about 200 nanometers from the waveguide thereby interacting with any bound reporter ligand within a distance of less than about 200 nanometers from the waveguide and resulting in a detectable signal.

In another embodiment, the present method provides an assay process including: injecting a solution including an biological target-containing sample and a reporter ligand into a sensor cell including recognition ligands bound to a film on a single mode planar optical waveguide, the film from the group of a membrane, a polymerized bilayer membrane, and a self-assembled monolayer containing polyethylene glycol or polypropylene glycol groups therein, both the recognition ligands and reporter ligands adapted for binding to selected biological targets; maintaining the biological target-containing sample within the sensor cell for a time sufficient for a binding event to occur between selected biological targets within the sample and the recognition ligands adapted for binding to selected biological targets and a time sufficient for a binding event to occur between selected biological targets within the sample and the reporter ligand; injecting a wash solution into the sensor cell to remove excess biological target and excess reporter ligand; and, interrogating the biological target-containing sample within the sensor cell with excitation light from the waveguide, the excitation light provided by an evanescent field of the single mode penetrating into the biological target-containing sample to a distance of less than about 200 nanometers from the waveguide thereby interacting with any bound reporter ligand within a distance of less than about 200 nanometers from the waveguide and resulting in a detectable signal.

BRIEF DESCRIPTION OF THE DRAWINGS

FIG. 5(A) and FIG. 5(B) show the reduction of nonspecific binding and standard curve for protective antigen detection. In order to eliminate nonspecific binding, and hence increase the sensing capability, streptavidin was substituted for avidin and the biotin-PE concentration was reduced from 3% to 1% biotin-PE in DOPC. In FIG. 5(a), the spectral response (top spectra) of the biosensor to repeated exposure of the detection antibody to the active surface (capture antibody, streptavidin, and bioactive membrane) is shown with the background subtracted spectra shown in the lower plot. The amount of nonspecific binding can be significantly decreased and thereby ultimately increase the sensitivity. In FIG. 5(b), the initial standard curve titrations for PA on SiONx waveguides are shown.

DETAILED DESCRIPTION

The present invention concerns sandwich assay processes using a single mode planar optical waveguide and thin film supported sandwich assay elements on a single mode planar optical waveguide. The use of sandwich assays on single mode waveguides takes advantage of the relatively high intensity of the evanescent field at the surface of the waveguide, as the detection molecules are well within the strong portion of the evanescent field, especially during the detection of a biological target such as proteins.

Figure 1:
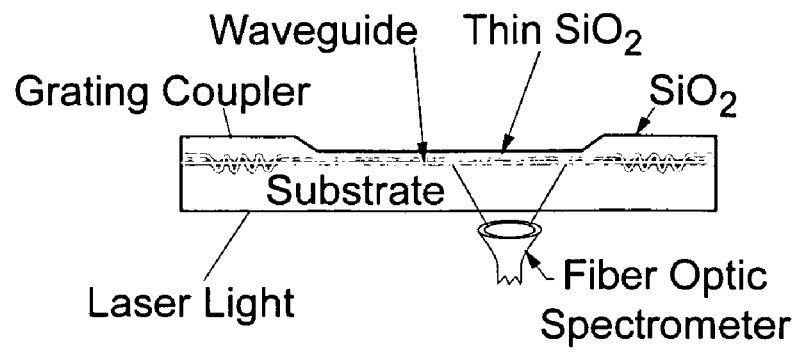
FIG. 1 shows a single mode waveguide in accordance with the present invention.

The base substrate in the present invention is a waveguide, preferably a single mode planar optical waveguide. Single mode waveguides can be generally formed from thin (generally from about 100 to 150 nm in thickness) high index of refraction dielectric materials deposited upon a substrate having a much lower refractive index. Use of a waveguide can eliminate some problems related to background autofluorescence from complex samples and Raman scattering from water. Preferably, the waveguide surfaces will be of a material that can be employed to attach an intervening thin film material, such materials including, e.g., silica, silicon nitride, titania, mixtures of silica and silicon nitride often referred to as SiON, and the like. The materials used for the waveguide can also be a sol-gel material. FIG. 1 shows a single mode waveguide where waveguide 10 includes substrate 12 with a thin silica coating 14. Laser light can be entered at 16 and coupled into the waveguide through grating coupler 18. A fiber optic spectrometer 20 can be positioned normal to waveguide 10 to collect emission from waveguide 10. Diffraction gratings, etched into the substrate, provide a facile method of coupling laser light into the thin waveguide film. Although most of the laser light is contained within the guided mode, a small portion (the evanescent field) extends out into the substrate and into the medium, which includes the biological sample. This evanescent filed falls off exponentially as the distance from the waveguide surface increases, and is effectively zero at a distance of less than half the wavelength of the coupled light.

Figure 2:
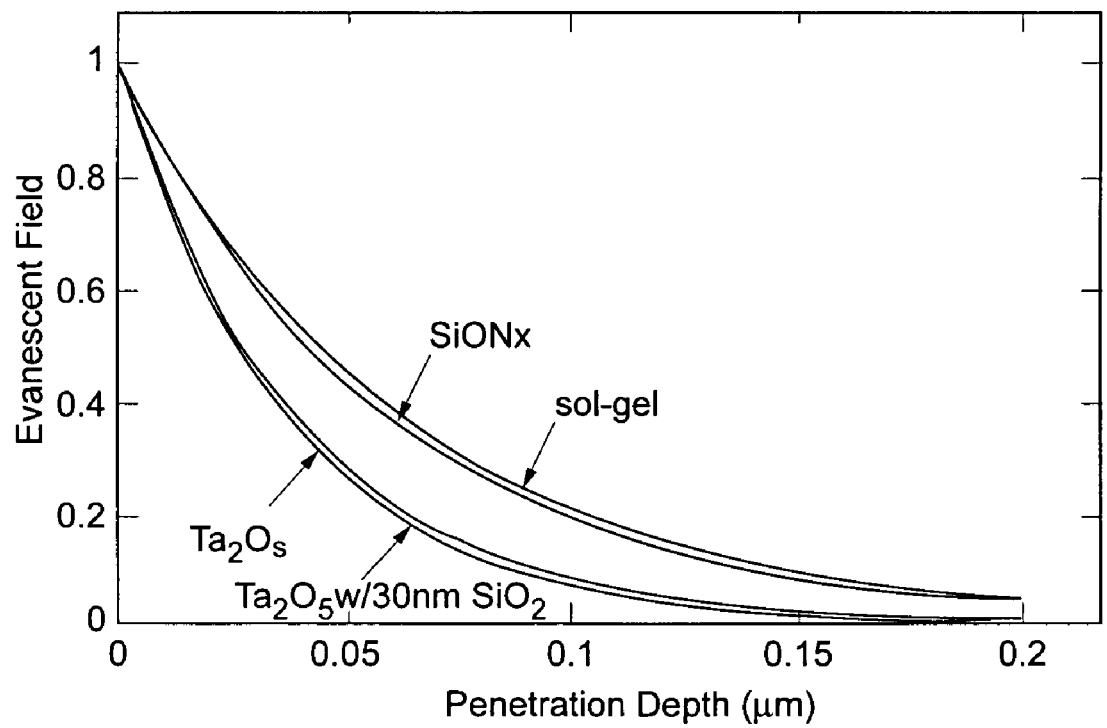
FIG. 2 shows normalized evanescent field decay for different waveguide materials. The calculations presented are for single mode slab (step index) waveguides where the thickness of the waveguide material is dictated by the index mismatch between the waveguide and the substrate, assuming a wavelength of 532 nm and TE polarization. All calculations were performed using a commercially available software package (BBV Software BV, Hengelosetstraat 705, 7251 PA Enschede, The Netherlands) based on the Complex Transfer Matrix or the Cauchy Integral method. In these calculations, an aqueous sample above the waveguides has been assumed

The decay of the evanescent field is depicted in FIG. 2 for sol-gel and $SiON_x$ materials. For comparison the behavior of the evanescent field for higher index $Ta_2O_5$ waveguides with and without a thin $SiO_2$ clad is also shown. The $SiO_2$ clad is used to facilitate deposition of either lipid bilayer membranes or self-assembled monolayer films that are needed as interfaces between the waveguide and the biological sample. The calculations presented in FIG. 2 are for single mode slab (step index) waveguides where the thickness of the waveguide material is dictated by the index mismatch between the waveguide and the substrate. As can be seen, the decay of the evanescent field is rapid and light does not penetrate into the sample beyond roughly 200 nm. In effect, this spatial filtering feature of single mode waveguides insures that little intrinsic fluorescence is excited within the biological sample, thereby minimizing background. Although the evanescent field does not penetrate far into the sample, the field strength at the surface where the biological detection takes place is very intense. This second attribute of single mode optical waveguides, the high relative intensity of the evanescent field at the active film surface, insures observation of very low concentrations of reporter dyes. It is noted that multimode or thick slab waveguides operating near the critical angle as used by other groups have 2-3 orders of magnitude lower optical field intensity at the waveguide surface and much deeper penetration of the evanescent field into the sample (about 1-2 µm)

The present invention involves the use of recognition ligands bound to a film on the base substrate or waveguide. By "recognition ligand" is meant any compound, composition, molecule or ligand capable of recognizing and having a binding affinity for a specific target such as a biomolecule. Natural recognition molecules include antibodies, enzymes, lectins and the like. For example, the recognition molecule for an antigen is an antibody while the recognition molecule for an antibody is either an anti-antibody or preferably, the antigen recognized by that particular antibody.

In sandwich assay sensors such as the present invention, recognition ligands are sometimes referred to as capture ligands. Among such ligands capable of recognizing and having a binding affinity for a specific target are biomolecules such as antibodies, antibody fragments, i.e., a portion of a full length antibody such as, e.g., Fab, Fab', F(ab')$_2$, or Fv fragments and the like, recombinant or genetically engineered antibody fragments, e.g., diabodies, minibodies and the like. Other suitable recognition ligands can include peptoids, single chain Fv molecules (scFv), peptides and mimetics thereof, carbohydrates, sugars and mimetics thereof, oligosaccharides, proteins, nucleotides and analogs thereof, aptamers, affinity proteins, small molecule ligands, and monomers of multimers of each, i.e., multidentate ligands. Mixtures of such recognition ligands may be used as well.

A recognition ligand can also be attached to a material that can be fluorescent, such as organic fluorophores, quantum dots or other fluorescent particles, or attached to silica or other suitable particles for scatter product detection. The attached material whether the fluorescent material or the material suitable for scatter product detection is often referred to as a reporter, e.g., a reporter ligand. Such attached materials provide a signaling function or a reporting function. The present invention also involves the addition of a recognition ligand/reporter ligand to the sensor system following reaction of the recognition or capture ligands with any target biomolecule. By "recognition ligand/reporter ligand" is meant a ligand capable of recognizing and having a binding affinity for a specific target such as a biomolecule, the ligand also providing the signaling or reporting function. Mixtures of such recognition ligand/reporter ligands may be used as well.

The recognition ligands and recognition ligand/reporter ligands are suitable for binding with selected biological targets from among the group of antigens, peptides, proteins, enzymes, hormones, vitamins, drugs, carbohydrates, nucleotides and the like. The selected biological target may also be from among the group of cells or cellular debris where the recognition ligand and recognition ligand/reporter ligands can bind to cell surface antigens or other cell surface features. Among suitable recognition ligands are included antibodies such as capture antibodies that can bind with selected antigen partners.

The base substrate includes a film thereon, the film being a bilayer membrane, a hydrid bilayer membrane, a polymerized bilayer membrane, or a self assembled monolayer (SAM) containing polyethylene glycol or polypropylene glycol groups therein. The term "polymerized membrane" refers to membranes that have undergone partial or complete polymerization. One example of a polymerized membrane can be polymerized phospholipids prepared from polymerizable monomeric groups as shown, e.g., in U.S. Pat. No. 6,699,952.

By "membrane" is generally meant supported bilayers where membrane layers are deposited upon a support surface, hybrid bilayers where a first layer is covalently attached to an oxide surface, tethered bilayers where a membrane molecule is covalently bonded to the oxide substrate, or bilayers cushioned by a polymer film. Supported membranes useful in the practice of the present invention are generally described by Sackmann, in "Supported Membranes: Scientific and Practical Applications", Science, vol. 271, no. 5245, pp. 43-45, Jan. 5, 1996.

A self assembled monolayer can be attached to the substrate as follows: solution or vapor deposition using siloxane groups such as octadecyltrichlorosilane (OTS) or by Langmuir-Blodgett assembly using a LB trough.

The lipid components that can be used for the membrane layers in the present invention are generally described in the literature. Generally, these are phospholipids, such as, for example, phosphatidylcholines, phosphatidylethanolamines, phosphatidylglycerols, phosphatidylserines, phosphatidic acids, phosphatidylinositols or sphingolipids.

The recognition ligands can be linked or bound through various molecules to the film on the waveguide surface. Among suitable linking molecules can be various biotin-avidin linkages such as biotinylated lipids, and trifunctional linker molecules as described by Schmidt et al., U.S. Ser. No. 10/104,158, "Generic Membrane Anchoring System", filed on Mar. 21, 2002, such description incorporated herein by reference. Such trifunctional linker molecules can include membrane anchoring groups where the film is a membrane. Such trifunctional linker molecules can be preferable where a reference dye is desired to be incorporated into the system by addition onto one arm of the trifunctional linker molecules. This can serve to minimize background by comparison with the dye label on the sandwich assay. Such trifunctional linkers may also have a secondary recognition ligand in addition to the primary recognition ligand. The use of a secondary recognition ligand that binds an orthogonal epitope relative to the primary recognition ligand can serve to enhance the effective binding affinity thereby increasing the overall sensitivity of the assay.

The sandwich assay process of the present invention can be widely used for the determination, either qualitative or, mostly, quantitative, of a nearly unlimited variety of biomolecules, either of natural origin or synthetic chemical compounds, such as peptides, proteins, enzymes, carbohydrates, antigens, cell surface antigens or cell surface features (in general, biomolecules that have recognition ligands and reporter ligands identified that are specific for such biomolecules). This waveguide-based sandwich assay could be for various purposes, including, e.g., diagnosis and monitoring of cancer, diagnosis and monitoring of infectious disease, monitoring of water quality or food quality, but also for forensic applications, and generally for any analytic purpose.

Assay sensitivities are partially determined by the affinity of the antibody for the antigen. It is desirable that sensitive antibodies should have a $K_d$ of at least 0.1-10 nM. The availability of two or more binding sites on a single antigen increases the apparent affinity of the interaction, by decreasing the off-rate of the antigen-antibody complex.

Formation of a bilayer membrane upon the waveguide surface can be accomplished by vesicle fusion, a process well known to those skilled in the art. Formation of either supported bilayer or hybrid bilayer membranes can also be accomplished using Langmuir-Blodgett techniques.

In the process of the present invention, dye-labeled reporter ligands are used to bring a dye reporter into the proximity of the interrogation field such that a signal can be obtained. Such reporter ligands are suitable for binding with the selected biological target following the binding of the selected biological target with the recognition ligand. Suitable reporter ligands can be antibodies that can bind with selected antigen partners.

Suitable dyes for the reporter ligand can include fluorophores such as, but not limited to, fluorescein, cadaverine, Texas Red™ (Molecular Probes, Eugene, Oreg.) and Cyanine 5™ (BDS, Pa.). Generally, any fluorophore will typically be detectable in the visible to near infrared range, although other ranges may be used as well. Quantum dots and nanoshell materials can also be used as reporter dyes, as can dye encapsulated silica particles. In addition, scatter molecules such as selected metal, semiconductor or magnetic nanoparticles attached to oligonucleotides as described, e.g., by Mirkin et al. in U.S. Pat. No. 6,903,207, such description incorporated herein by reference, may be used as well.

Interrogation of the sandwich assay in the process of the present invention is generally conducted at specific wavelengths selected to minimize or substantially eliminate background signal. By using the evanescent field from the waveguide, excitation light for the dye will only penetrate a short distance into the sample, generally less than about 200 nm. Within that distance, any bound biological target would also have the reporter ligand attached, but background would be minimized as little or no unbound dye label would be present.

The sensor and process of the present invention can provide high sensitivities and specificities. In some instances, detection of biological targets at levels as low as from about 100 femptomolar (fM) to about 1 pM can be obtained.

Figure 3:
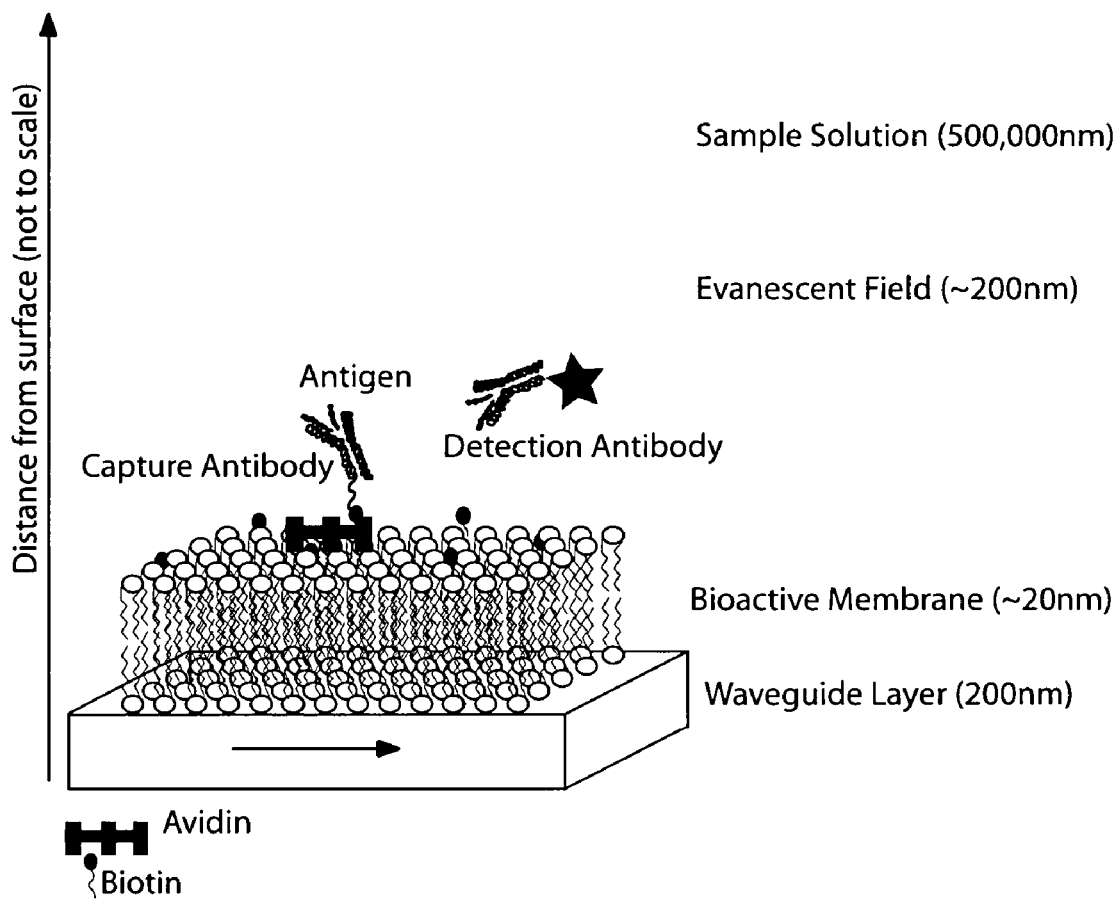
FIG. 3 illustrates a membrane-based sandwich assay where a recognition ligand, e.g., a capture antibody, is conjugated to a lipid molecule that anchors the antibody to the upper surface of a lipid bilayer. Exposure to an antigen (A) followed by a wash step and exposure to a fluorescent labeled reporter ligand results in formation of the sandwich.

In one embodiment of the present invention, capture antibodies (as the recognition ligands) are conjugated to membrane anchoring molecules that anchor the capture antibodies to the upper fluid leaf of a phospholipid bilayer coating the surface of a single mode planar optical waveguide (see FIG. 3). Although shown configured using a fluid membrane, self assembled monolayers or other stable supported architectures such as polymerized bilayer membranes could be utilized as well. Laser excitation is coupled into the single mode waveguide through a grating structure that is imbedded onto the waveguide/substrate interface. A sample containing the biological target to be detected, i.e., protective antigen (PA), is then injected into the cell and allowed to incubate for a brief period of time (about 5 minutes) to permit binding of the biological target to the capture antibody. The sample is then replaced with buffer solution to wash away excess antigen. This wash step is followed by injection of a buffer solution containing a reporter ligand that has been labeled with a fluorescent molecule, e.g., an organic dye, an inorganic dye, a quantum dot or the like. The excitation light from the evanescent field of the single mode guided by the waveguide only penetrates a short distance (less than about 200 nm) into the sample, but this is adequate to excite the dye on the reporter ligand generating a fluorescence signal that is then detected, e.g., by a miniaturized fiber optic spectrometer that images the waveguide streak. In the absence of detectable antigen, little or no signal is generated in the spectral region of the reporter fluorescence.

Figure 4:
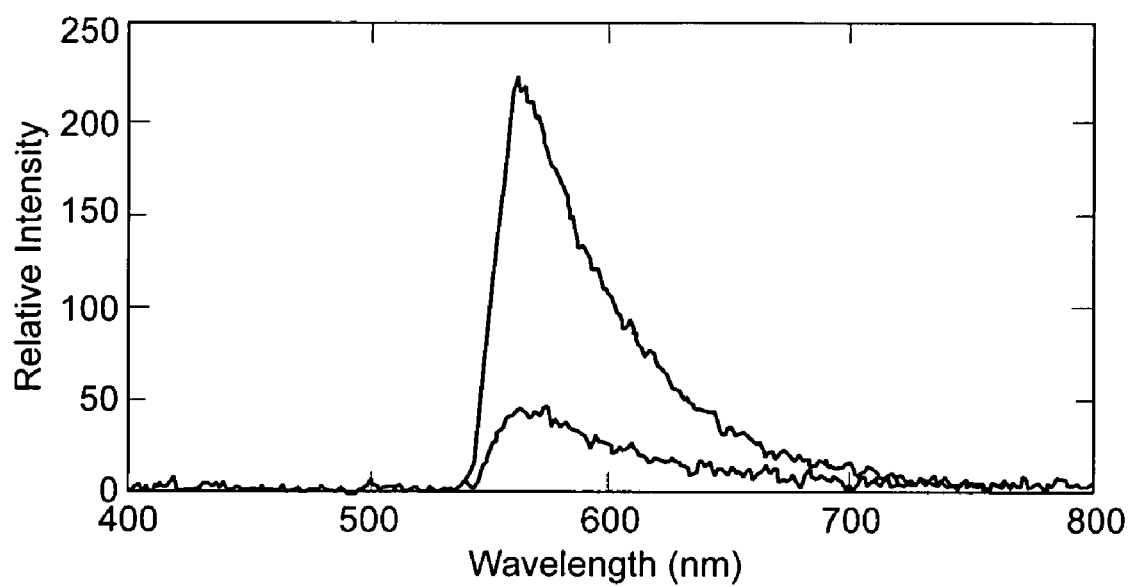
FIG. 4 shows a graph of the spectral response of a membrane sandwich assay on a waveguide surface in accordance with the present invention to a sample containing 1 pM protective antigen. Biotinylated capture antibodies were coupled through avidin to biotinylated phospholipid bilayer composed of 3% biotin-PE in a matrix of DOPC and attached to the surface of the sol-gel planar optical waveguide. The top curve shows the spectral response of the excited waveguide following exposure to a complex medium spiked with 1 pM (0.083 ng/mL) PA. The lower curve is the response observed for the same membrane/waveguide structure when exposed to complex medium, which did not contain PA, followed by exposure to detection antibody. This response represents the background and nonspecific signal.

In one embodiment, the present invention can be operated using a bench-top waveguide-based sensor system as described by Grace et al. in U.S. Pat. No. 6,801,677, "Waveguide-Based Optical Chemical Sensor", such description incorporated herein by reference. In another embodiment, the present invention can be operated using an optical waveguide-based biosensor system as described by Grace et al. in U.S. Ser. No. 10/842,750, "Integrated Optical Biosensor System", filed on May 11, 2004, such description incorporated herein by reference. The present invention can measure antigen, e.g., PA, present in a buffer or serum, e.g., biological materials or environmental sample. Measurements can be performed using suitable recognition ligands and recognition ligand/reporter ligands for the target markers such as antigen or oligonuceotide. Different spectral response is expected for different samples as shown in FIG. 4. In each of these measurements, the incubation times for exposure to the sample and subsequent exposure to a recognition ligand/reporter ligand can be limited to five minutes each. The overall assay can be performed in as little as 10 minutes using the automated system. It is noteworthy to compare the results obtainable by the present invention to the results of commercial ELISA methods. The commercial ELISA assay takes at least 3 to 5 hours whereas the waveguide-based assay of the present invention can be completed in less than about 10 minutes.

In the preparation of the membrane sandwich assay structure in accordance with the present invention, the recognition ligand (capture antibody) can be anchored to the surface of a membrane using a biotin-avidin sandwich prepared as follows. The capture antibody can be conjugated to biotin using a biotin-ester molecule such as EZ-link Sulfo-NHS-LC-LC-biotin (commercially available from Pierce). A membrane can be fused onto the surface of the waveguide from a lipid mixture including, e.g., 1,2-Dioleoyl-sn-Glycero-3-Phosphocholine (DOPC) and a biotinylated lipid such as 1,2-Dipalmitoyl-sn-Glycero-3-Phosphoethanolamine-N-(Biotinyl) (commercially available from Avanti Polar Lipids) using standard vesicle fusion techniques. The membrane on the waveguide surface can then be exposed to a solution of avidin and allowed to incubate for 5 minutes. Following rinsing by PBS, the biotinylated antibody can be added and incubated for 5 minutes. A sample cell containing the active membrane can then be ready for exposure to a sample.

One embodiment of the sensor system involves a portable test-bed system. As a light source, a stabilized diode pumped 532 nm frequency doubled yttrium orthovanadate laser or a 635 nm diode laser was used. Grating couplers were used for a facile method of coupling excitation light into the thin waveguide material. Laser light was coupled into the waveguide by positioning the excitation beam onto the diffraction grating at the appropriate angle of impingement. This angle can be determined by the effective mode index of the waveguide film, film thickness, and the period and amplitude of the grating structure. These parameters were adjusted to provide a 10-degree input coupling angle for an excitation wavelength of 532 nm.

A USB 2000 fiber optic spectrometer (Ocean Optics, Dunedin, Fla.) was positioned normal to the waveguide surface to collect the isotropic emission from the waveguide (see FIG. 1). A long pass filter was used to filter out the excitation light. All optical components were mounted onto a 12 inch by 12 inch by 0.5 inch optical bench. The test bed allows the simple removal and installation of the sample cartridge without realignment of the optical train. The final component of this system was a PC based user interface for instrument control, data acquisition and analysis. The portable system permits precise measurements against various protein markers in virtually any laboratory setting.

The waveguide was coated with lipid membranes having biotin-avidin conjugated antibodies in the upper fluid leaf and was placed within a simple fluid cell. This cell was mounted in the sample cartridge and was irradiated as generally described above. An Ocean Optics fiber optic spectrometer was used, and it was positioned normal to the waveguide surface to collect the isotropic emission from the waveguide. The optical components were mounted onto a 12 inch by 12 inch by 0.5 inch optical bench. The test bed allowed the simple removal and installation of the sample cartridge without realignment of the optical train. The final component of this system was a PC based user interface for instrument control, data acquisition and analysis. Such a portable system permits precise measurements against various pathogens and protein markers.

The present invention is more particularly described in the following examples which are intended as illustrative only, since numerous modifications and variations will be apparent to those skilled in the art.

1,2-Dioleoyl-sn-Glycero-3-Phosphocholine (DOPC) and 1,2-Dioleoyl-sn-Glycero-3-Phosphoethanolamine-N-(Cap Biotinyl) (cap-biotin-PE) were purchased from Avanti Polar Lipids, Inc., Alabaster, Ala.

Protective antigen (PA) was purchased from RDI, Division of Fitzgerald Industies, Concord, Mass.

Anti-PA antibodies (BAP0106, BAP0105, BAP0103, BAP0102, C3) were purchased from Advanced ImmunoChemical Inc., Long Beach, Calif.

Antibodies against *Bacillus anthracis* cells were purchased from Tetracore, Inc., Gaithersburg, Md.

*B. anthracis* vegetative cells were prepared as described previously by Mendelson et al., Microb. Pathog., vol. 37, pp. 149-154 (2004). Cells were used in assays as a 10-fold dilution of $10^6$ cfu/mL concentration.

EZ-Link Sulfo-NHS-LC-LC-Biotin, streptavidin, and avidin were purchased from Pierce Chem. Co., Rockford, Ill.

Alexa Fluor® 532 and 647 were purchased from Molecular Probes, Inc., Eugene, Oreg.

Phosphate buffered saline (PBS), at a concentration of 1×, bovine serum albumin (BSA), and 3,3',5,5'-Tetramethylbenzidine (TMB) were purchased from Sigma-Aldrich. Pairs of monoclonal antibodies specific for *B. anthracis* were either biotinylated (for capture as recognition ligands) or labeled with Alexa Fluor® 532 or 647 (for detection as reporter ligands). Conjugated antibodies were purified using a Sephadex G-50 column and exhaustive dialysis against PBS, and were tested for binding activity (ELISA) and the extent of biotinylation or fluorescent labeling. Antibodies were generally labeled at no more that an average of three fluorescent dyes/antibody molecule. The degree of fluorescent labeling was particularly important for BAP0106 (anti-PA). Four pairs of anti-PA monoclonal antibodies were tested where each antibody in the pair was used as either a capture antibody or a detection antibody. Differences in the performance of the antibodies on planar waveguides were not as distinct as the differences observed by ELISA. The antibody pair BAP0105 and BAP0106 performed best in waveguide assays and was chosen for use in further studies. Each antibody worked equally well for either capture or detection.

Sol-gel based planar optical waveguides can be made in accordance with the description of Yang et al., "Fabrication and Characterization of Low-Loss, Sol-Gel Planar Waveguides, Anal. Chem, vol. 66, pp. 1254-1263 (1994), such description incorporated herein by reference. SiONx planar optical waveguides can be obtained from nGimat Co., Atlanta, Ga.

Unilamellar vesicles were prepared by sonication as previously described by Xu et al., J. Amer. Chem. Soc., vol. 124, pp. 13408-13415 (2002), such description incorporated herein by reference. Thin films of DOPC and 1% cap-biotin-PE were deposited on the side walls of 5 mL test tubes by evaporation of the chloroform solution under a stream of argon gas. The lipid films were incubated and hydrated in PBS at room temperature for 30 minutes, and then the mixture was sonicated with a probe tip sonicator for six minutes.

Sol-gel planar waveguides and glass microscopy slides were sonicated in chloroform, methanol, and then water for five minutes each. The sol-gel waveguides were subsequently Piranha etched (1:4 parts solution of 30% hydrogen peroxide and sulfuric acid, 110° C.) for two minutes and transferred to a bath of ultra-pure water (18M Ohm). SiONx planar waveguides were either cleaned as described above or by solvent sonication followed by exposure to UV-ozone for a period of 10-20 minutes and a final wash with ultra-pure water. This later treatment for SiONx waveguides was found preferential to using Piranha etch in order to prevent pitting of the surface and subsequent light loss in guiding. The waveguides were assembled into a flow cell, as described previously by Grace et al. Proc. SPIE-Int. Soc. Opt. Eng. Vol. 5269, pp. 55-64 (2004), such description incorporated herein by reference. A supported lipid bilayer was formed on the waveguide surface, and the glass slide, by injecting the vesicle solution into the flow cell and incubating overnight. The resulting membrane was then rinsed with either 2% BSA-PBS or PBS.

A generic conjugation method was utilized to link the capture antibody to the waveguide surface. Streptavidin or avidin was added to the cap-biotin-PE/DOPC membrane and allowed to incubate for five minutes. The flow cell was rinsed with 0.5% BSA-PBS and capture antibody was added and incubated for five minutes. The cells were blocked either before or after addition of the avidin with 2% BSA-PBS for 1 hour.

Planar waveguide measurements were carried out as follows. Spiked PA samples (pM-µM), and detection antibody were sequentially added to the preformed biosensor surface and individually incubated for five minutes. Rinses consisting of 0.5% BSA-PBS were completed after each addition. Samples containing the spiked PA were tested in different matrices (either PBS, 2% BSA, or a complex medium consisting of 20% (wt/wt) crude amino acids, 9% (wt/wt) NaCl, and bacterial cellular debris). The sample matrix made little difference in the binding reactivity at high concentrations of PA (>1 nM). The detection antibody was excited (532 or 647 nm) and the emission (whole spectra) detected by a miniaturized fiber optic spectrometer coupled to the existing optical waveguide test bed instrument. Buffer samples (PBS and 0.5% BSA or complex medium) without PA were used as negative controls. Both the negative and positive controls were exposed to the detection antibody.

For use of the automated system, each sample (volume=1.25 ml) was flowed into the cartridge at a flow rate of 0.5 ml per minute via a four channel peristaltic pump (Ismatec, Switzerland). Each sample delivery was controlled by solenoid operated pinch valves (Bio-Chem Valve Inc., Boonton, N.J.). The pump and valves were all computer controlled by LabView software.

EXAMPLE 1

Biotinylated capture antibodies were coupled through avidin/streptavidin to biotinylated phospholipid bilayers composed of 1% to 3% biotin-phosphoethanolamine in a matrix of DOPC (1,2-Dioleoyl-sn-Glycero-3-Phosphocholine) and attached to the surface of planar optical waveguides. The performance of the immunoassay was evaluated by monitoring the response of the waveguide apparatus to varying concentrations of PA (pM to µM). No significant differences between the sensitivity of the instrumentation when PA was in buffer or in complex medium consisting of sugars, proteins, and cellular debris were observed. Although this assay has not yet been optimized for sensitivity, results from 1 pM PA (0.083 ng/mL, 0.0166 ng) in complex medium on sol-gel waveguides (FIG. 4) are shown. The top curve of this figure shows the spectral response of the excited waveguide following exposure to the complex medium spiked with 1 pM (0.083 ng/mL) PA. The lower curve is the response observed for the same membrane/waveguide structure when exposed to the complex medium, which did not contain PA, followed by exposure to the detection antibody. This response represents the background signal and the signal from detection antibody that is non-specifically bound to the membrane surface, to the capture antibody, or to avidin. The signal obtained for 1 pM PA (0.083 ng/mL) spiked into complex medium was more than twice that of nonspecific signal and the assay (10 minutes) was five hours shorter than the comparable ELISA. At no time was a hook effect, or false-negative signal, observed at high concentrations (mM).

Figure 5A:
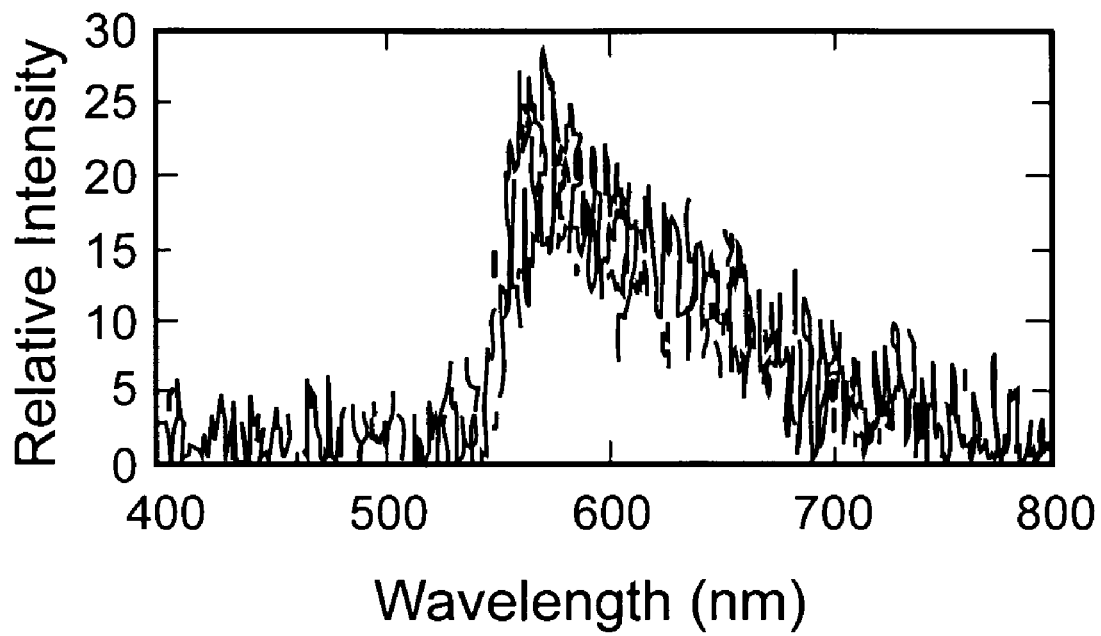
Figure 5A:
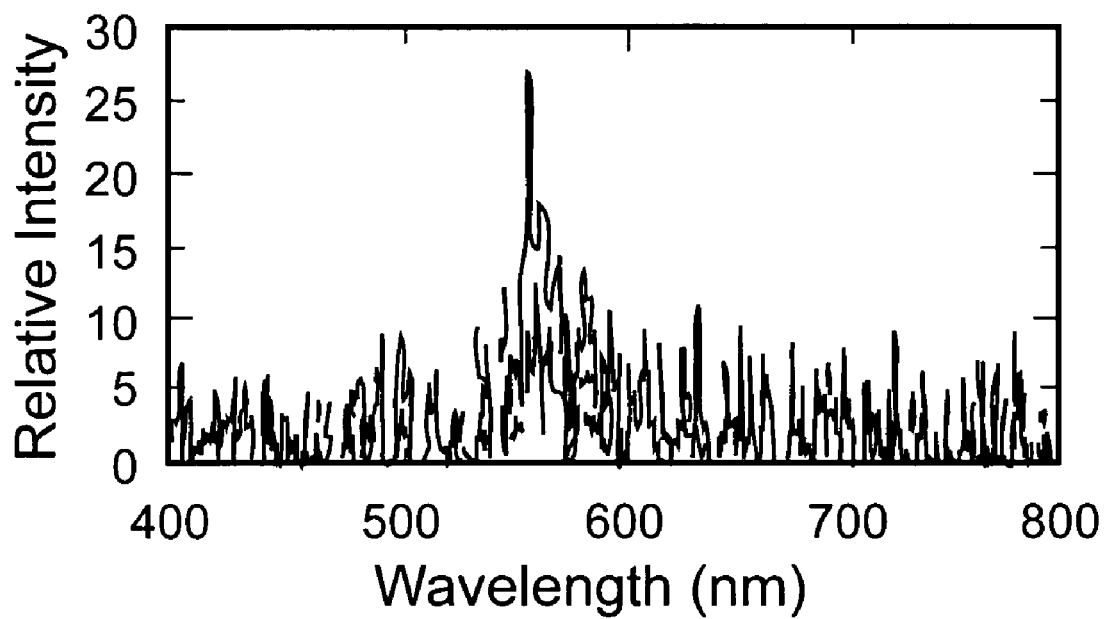
Figure 5B:
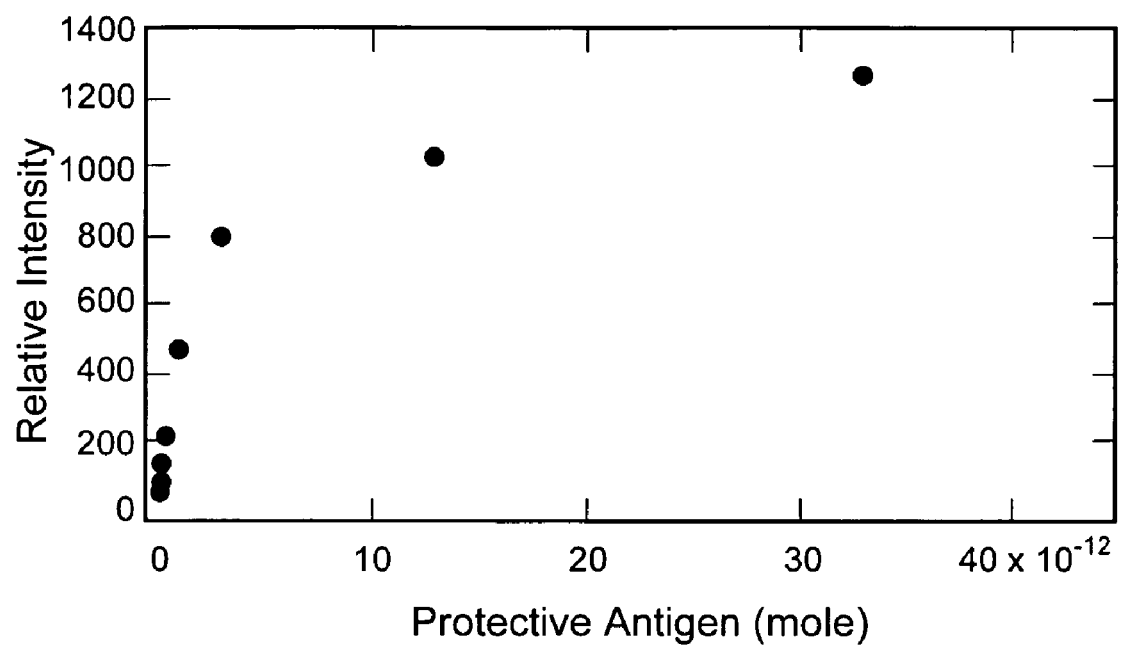

The sensitivity limit of the waveguide assay depends on the ability to measure a signal from specific versus nonspecific binding and background. This detection limit can be lowered by either reducing the nonspecific binding/background or by introducing a reference channel and reference dye to measure the signal generated by nonspecific binding. Following the development of this assay, streptavidin was substituted for avidin, and the concentration of biotin-PE decreased from 3% to 1%, further reducing the amount of nonspecific binding (FIG. 5(a)) observed in FIG. 4. As seen in FIG. 5(a), repeated exposure of the detection antibody to the streptavidin/capture antibody surface did not increase the amount of nonspecific binding and the level of nonspecific binding was not much higher than background. These results show that the amount of nonspecific binding can be significantly decreased and these experiments serve as controls for subsequent concentration curve titrations. Initial standard curves were completed for PA on SiONx waveguides (FIG. 5(b)). With the current waveguides and membrane architectures, saturation is reached at approximately 6 µg PA. However, this is a lower limit estimation of the linearity as the sequential addition of detection antibody following addition of increasing concentrations of PA results in PA binding sites that are not titratable (i.e., some PA binds to the second detection antibody binding site, and these events are not reported). Some differences in type of waveguide (sol-gel vs. SiON) limited the dynamic range.

Ultimately, it is expected that uniform and reproducible sensing films and low background waveguides can be formed to permit accurate measurement of the signal from nonspecific binding. In this way, the signal from nonspecific binding can be subtracted thereby giving higher sensitivity. However, the lowest level of detection for PA already exceeds that of other PA biosensors and ELISA formats. It is noted that the sensitivity of biosensors was dependent on not only the instrumentation, but on the affinity of the recognition molecules. Past attempts at developing PA sensors could have utilized low affinity antibodies, therefore decreasing the ultimate sensitivity of that detection platform; however, the affinity of the antibodies utilized in this study was also low (11±3 nM). Decreasing the level of nonspecific binding and background, and assuming a signal three times the deviation in nonspecific binding measurements, a sensitivity of 250 fM for PA in complex medium can be projected. Current evidence, based on animal studies, suggests that protective antigen concentrations could exceed 0.01-0.1 µg/mL (120 pM to 1.2 nM) in the blood of infected individuals during the acute stage of disease development. The present sensitive assay may therefore be useful to detect concentrations of PA found in early infection.

EXAMPLE 2

The present invention has also been targeted towards detection of *B. anthracis* cells. These results show that not only can the present invention detect pathogenic antigens, but also can detect cellular components. Whether cell detritus or whole cells are being detected is not wholly clear, as the majority of a whole cell captured on a waveguide surface would be beyond the evanescent field. Moreover, it is expected that capture of whole cells at the waveguide surface will be limited owing to slow diffusion of intact cells relative to smaller cell components from disrupted cells. Again, as stated earlier, whole cell or cellular debris detection in serum might be an alternative to cell culturing and fluorescent microscopy assays commonly used as definitive diagnostic tests. To add to this *B. anthracis* biosensor, an assay to detect capsule, encoded by one of the virulent plasmids of *B. anthracis*, is being incorporated. This is an important component for medical diagnostics.

Although the present invention has been described with reference to specific details, it is not intended that such details should be regarded as limitations upon the scope of the invention, except as and to the extent that they are included in the accompanying claims.

What is claimed is:

1. A sandwich assay sensor element comprising: recognition ligands bound to a film on a single mode planar optical waveguide, said film selected from the group consisting of a membrane, a polymerized bilayer membrane, and a self-assembled monolayer containing polyethylene glycol or polypropylene glycol groups therein.

2. The sandwich assay sensor element of claim 1 wherein the recognition ligands are selected from the group consisting of capture antibodies, antibody fragments, peptoids, carbohydrates, peptides, aptamers, affinity proteins, oligonucleotides, and small molecule ligands.

3. The sandwich assay sensor element of claim 1 wherein the membrane is a supported bilayer membrane.

4. The sandwich assay sensor element of claim 1 wherein the recognition ligands are bound to the film by trifimctional anchoring molecules including a fluorescent reporter molecule thereon.

5. The sandwich assay sensor element of claim 1 wherein the film is a membrane and the recognition ligands are bound to the film by trifunctional membrane anchoring molecules including a fluorescent reporter molecule thereon.

6. The sandwich assay sensor element of claim 1 wherein the film is a membrane and the recognition ligands are bound to the film by trifunctional membrane anchoring molecules including a secondary recognition ligand thereon.

7. The sandwich assay sensor element of claim 1 wherein the recognition ligands are movably situated within a fluid membrane through multifunctional membrane anchoring molecules.

8. The sandwich assay sensor element of claim 1 wherein the recognition ligands are for a biological target selected from the group consisting of antigens, peptides, proteins, enzymes, oligonucleotides, small organic molecules, cell surface markers and cellular debris.

9. The sandwich assay sensor element of claim 1 wherein the recognition ligands are for a biological target of an antigenic marker for a pathogen.

10. A sandwich assay process for detecting the presence of a biological target comprising:

injecting a biological target-containing sample into a sensor cell including recognition ligands bound to a film on a single mode planar optical waveguide, said film selected from the group consisting of a membrane, a polymerized bilayer membrane, and a self-assembled monolayer containing polyethylene glycol or polypropylene glycol groups therein, the recognition ligands capable of binding to selected biological targets;

maintaining the biological target-containing sample within the sensor cell for a time sufficient for a binding event to occur between selected biological targets within the sample and the recognition ligands capable of binding to selected biological targets;

injecting a solution including a reporter ligand into the sensor cell; and, interrogating the biological target-containing sample within the sensor cell with excitation light from the waveguide, the excitation light provided by an evanescent field of the single mode penetrating into the biological target-containing sample to a distance of less than about 200 nanometers from the waveguide thereby interacting with any bound reporter ligand within a distance of less than about 200 nanometers from the waveguide and resulting in a detectable signal.

11. The process of claim 10 wherein the recognition ligands are selected from the group consisting of capture antibodies, antibody fragments, peptoids, carbohydrates, peptides, aptainers, affinity proteins, oligonucleotides, and small molecule ligands.

12. The process of claim 10 wherein the membrane is a supported bilayer membrane.

13. The process of claim 10 further including injecting a wash solution into the sensor cell to remove excess biological target after the sample is maintained for time sufficient for a binding event to occur.

14. The process of claim 10 wherein the recognition ligands are bound to the film by trifunctional anchoring molecules including a fluorescent reporter molecule thereon.

15. The process of claim 10 wherein the film is a membrane and the recognition ligands are bound to the film by trifunctional membrane anchoring molecules including a fluorescent reporter molecule thereon.

16. The process of claim 10 wherein the film is a membrane and the recognition ligands are bound to the film by trifunctional membrane anchoring. molecules including a secondary recognition ligand thereon.

17. The process of claim 10 wherein the recognition ligands are movably situated within a fluid membrane through multifunctional membrane anchoring molecules.

18. The process of claim 10 wherein the biological target is selected from the group consisting of antigens, peptides, proteins, enzymes, oligonucleotides, small organic molecules, cell surface markers and cellular debris.

19. The process of claim 10 wherein the biological target is an antigenic marker for a pathogen.

20. The process of claim 10 wherein the reporter ligands include attached materials for fluorescence or scatter product detection.

21. A sandwich assay process for detecting the presence of a biological target including:

injecting a solution including a biological target-containing sample and a reporter ligand into a sensor cell including recognition ligands bound to a film on a single mode planar optical waveguide, said film selected from the group consisting of a membrane, a polymerized bilayer membrane, and a self-assembled monolayer containing polyethylene glycol or polypropylene glycol groups therein, the recognition ligands capable of binding to selected biological targets;

maintaining the biological target-containing sample within the sensor cell for a time sufficient for a binding event to occur between selected biological target within the sample and the recognition ligands capable of binding to selected biological targets;

injecting a wash solution into the sensor cell to remove excess biological target and excess reporter ligand; and, interrogating the biological target-containing sample within the sensor cell with excitation light from the waveguide, the excitation light provided by an evanescent field of the single mode penetrating into the biological target-containing sample, to a distance of less than about 200 nanometers from the waveguide thereby interacting with any bound reporter ligand within a distance of less than about 200 nanometers from the waveguide and resulting in a detectable signal.

22. The process of claim 21 wherein the recognition ligands are selected from the group consisting of capture antibodies, antibody fragments, peptoids, carbohydrates, peptides, aptamers, affinity proteins, oligonucleotides, and small molecule ligands.

23. The process of claim 21 wherein the membrane is a supported bilayer membrane.

24. The process of claim 21 wherein the recognition ligands are bound to the film by trifuctional anchoring molecules including a fluorescent reporter molecule thereon.

25. The process of claim 21 wherein the film is a membrane and the recognition ligands are bound to the film by trifunctional membrane anchoring molecules including a fluorescent reporter molecule thereon.

26. The process of claim 21 wherein the film is a membrane and the recognition ligands are bound to the film by trifunctional membrane anchoring molecules including a secondary recognition ligand thereon.

27. The process of claim 21 wherein the recognition ligands are movably situated within a fluid membrane through multifunctional membrane anchoring molecules.

28. The process of claim 21 wherein the biological target is selected from the group consisting of antigens, peptides, proteins, enzymes, oligonucleotides, small organic molecules, cell surface markers and cellular debris.

29. The process of claim 21 wherein the reporter ligands include attached materials for fluorescence or scatter product detection.

30. The process of claim 21 wherein the biological target is an antigenic marker for a pathogen.

* * * * *